(12) United States Patent
Yasuhara et al.

(10) Patent No.: US 6,593,484 B2
(45) Date of Patent: Jul. 15, 2003

(54) TANTALUM TERTIARY AMYLIMIDO TRIS (DIMETHYLAMIDE), A PROCESS FOR PRODUCING THE SAME, A SOLUTION OF STARTING MATERIAL FOR MOCVD USING THE SAME, AND A METHOD OF FORMING A TANTALUM NITRIDE FILM USING THE SAME

(75) Inventors: Sakiko Yasuhara, Hatoyama-machi (JP); Hidekimi Kadokura, Tokyo (JP)

(73) Assignee: Kabushikikaisha Kojundokagaku Kenkyusho, Saitama (JP)

( * ) Notice: Subject to any disclaimer, the term of this patent is extended or adjusted under 35 U.S.C. 154(b) by 75 days.

(21) Appl. No.: 10/037,737

(22) Filed: Nov. 9, 2001

(65) Prior Publication Data

US 2002/0115886 A1 Aug. 22, 2002

(30) Foreign Application Priority Data

Dec. 25, 2000 (JP) ........................ 2000-404625

(51) Int. Cl.$^7$ ............................ C07F 9/00; H01L 21/44; C23C 8/54
(52) U.S. Cl. ........................ 556/42; 438/681; 427/590; 501/96.2
(58) Field of Search .......................... 556/42; 501/96.2; 427/590; 438/681

(56) References Cited

U.S. PATENT DOCUMENTS 5,668,054 A * 9/1997 Sun et al. ................... 438/653
6,015,917 A * 1/2000 Bhandari et al. ............. 556/12

* cited by examiner

*Primary Examiner*—Porfirio Nazario-Gonzalez
(74) *Attorney, Agent, or Firm*—Fattibene & Fattibene; Paul A. Fattibene; Arthur T. Fattibene

(57) ABSTRACT

A stable compound having a vapor pressure higher by 1 order than that of $Ta(NtBu)(NEt_2)_3$ is provided as a starting material for forming a TaN film as a barrier film by the CVD method. There are further provided a process for producing the same and a method of forming a TaN film by using the same. The novel compound, tantalum tertiary amylimido tris(dimethylamide) $[Ta(NtAm)(NMe_2)_3]$ has a vapor pressure of 1 Torr at 80° C., and its melting point is 36° C. This compound is obtained by allowing 1 mole of $TaCl_5$, 4 moles of $LiNMe_2$ and 1 mole of LiNHtAm to react with one another in an organic solvent in the vicinity of room temperature, then separating byproducts by filtration, distilling the solvent away, and distilling the product in vacuo. This compound can be used as a starting material in CVD to form a cubic TaN film on a $SiO_2$/Si substrate at 550° C. at 0.05 Torr.

4 Claims, 4 Drawing Sheets

TANTALUM TERTIARY AMYLIMIDO TRIS (DIMETHYLAMIDE), A PROCESS FOR PRODUCING THE SAME, A SOLUTION OF STARTING MATERIAL FOR MOCVD USING THE SAME, AND A METHOD OF FORMING A TANTALUM NITRIDE FILM USING THE SAME

BACKGROUND OF THE INVENTION

1. Field of the Invention

The present invention relates to a tantalum compound suitable for forming, by the MOCVD method, a tantalum nitride film serving as a ground barrier in forming a copper film on semiconductor devices, a process for producing the same, and a method of forming a tantalum nitride film using the same.

2. Description of the Related Art

It is known that tantalum nitride is very effective as a ground barrier on semiconductor devices. For further thinning copper paths for electric current, further thinning of this barrier film is also required, and formation of a tantalum nitride film by the CVD method superior in mass-productivity and in the step coverage ability came to be necessary.

U.S. Pat. No. 5,668,054 discloses a CVD method using tantalum tertiary buthylimido tris(diethylamide) $Ta(NtC_4H_9)(N(C_2H_5)_2)_3$ (referred to hereinafter as $Ta(NtBu)(NEt_2)_3$ as the starting material, wherein a low-resistant tantalum nitride film is formed on a substrate at 450 to 650° C. in a low-pressure reaction chamber of cold wall type at 0.02 Torr. The film at 600° C. is preferable with resistance as low as 600 $\mu\Omega$·cm, and even upon treatment at a high temperature of 500° C., can prevent copper diffusion and significantly lower leak current.

The starting material $Ta(NtBu)(NEt_2)_3$ is liquid at room temperature, and is supplied after gasification by heating at a source temperature of 40 to 50° C.

In Appl. Phys. Lett., vol. 67(8)1128 (1995), the inventors of said prior art patent estimated that low-resistant cubic TaN could be formed because Ta=NtBu in the starting compound, that is, the strong bond of Ta=N was preserved and integrated in the cubic system. Before publication of said literature, said inventors disclosed in J. Mater. Sci. Lett., vol. 11, 96 (1992) that low-carbon cubic TaN was formed by CVD of $Ta(NEt)(NEt_2)_3$, but because a pure material of $Ta(NEt)(NEt_2)_3$ was hardly obtained, said inventors used $Ta(NtBu)(NEt_2)_3$ in place of $Ta(NEt)(NEt_2)_3$.

R. M. Fix, R. G. Gordon and D. M. Hoffman, in Chem. Mater., vol. 5, 614 (1993), have reported that cubic $Ta_3N_5$ film of high resistance (>$10^6$ $\mu\Omega$·cm) was formed in CVD using tantalum pentakis(dimethylamide) $[Ta(NMe_2)_5]$ and ammonia.

U.S. Pat. No. 6,015,917 claims 10 groups of compounds having Ta—N and/or Ta=N bond as the starting material in CVD for forming a tantalum nitride film, as well as solutions thereof in hexane or toluene. In (viii), claim 1 describes, but does not specify, $Ta(NR_1)(NR_2R_3)_3$ wherein $R_1$, $R_2$ and $R_3$ are independently from H, $C_1$–$C_8$ alkyl, aryl, $C_1$–$C_8$ perfluoroalkyl, and silicon-containing groups selected from the group consisting of silane, alkyl silane, perfluoroalkylsilyl, triaryl silane and alkylsilyl silane. This patent specification describes, in the Examples, only one compound of tantalum pentakis(dimethylamide) [Ta(NMeEt)$_5$], and does not contain any description of the conditions for forming the film and the physical properties of the film.

JP-A 2000-204095 also discloses that a tantalum nitride film was formed from Ta(NMeEt)$_5$ or a solution thereof in organic solvent and an ammonia gas at a substrate temperature of 450° C. at a pressure of 10 Torr, but there is no description of the crystalline form of said film.

As described above, low-resistant cubic TaN has been obtained until now from only tantalum alkylimido tris (dialkylamide) having Ta=N.

It is generally preferable that at the time of supply, the starting compound in CVD for mass-production has such properties that it is a pure material, has high vapor pressure, is thermally stable at the time of supply, and is liquid in the vicinity of room temperature or at least at the temperature of a source used. From these viewpoints, $Ta(NtBu)(NEt_2)_3$ in U.S. Pat. No. 5,668,054 is disadvantageous in that its vapor pressure is not high because of high molecular weight. According to measurement of vapor pressure by the present inventors, the vapor pressure thereof was 1 Torr/130° C.

According to measurement of vapor pressure by the present inventors, a similar known compound, tantalum tertiary buthylimido tris(dimethylamide) $[Ta(NtC_4H_9)(N(CH_3)_2)_3]$ has a vapor pressure of 1 Torr/70° C. which is higher than that of $Ta(NtBu)(NEt_2)_3$, but the problem of this compound is its melting point as high as 69° C. For a usual liquid mass flow controller, the temperature which can be kept by heating for melting a starting compound is about 50° C., and thus $Ta(NtBu)(NMe_2)_3$ with a melting point of 69° C. is not suitable. The material desirably has a melting point in the vicinity of room temperature or about 40° C. or less.

SUMMARY OF THE INVENTION

The present invention provides a novel compound having a higher vapor pressure than that of $Ta(NtBu)(NEt_2)_3$, a melting point of 40° C. or less, and Ta=N bond, as well as a process for producing the same. Further, the present invention provides a method of forming a cubic TaN film by using the same in the CVD method.

According to one aspect of the present invention, there is provided a novel compound, tantalum tertiary amylimido tris (dimethylamide).

According to another aspect of the present invention, there is provided a process for producing tantalum tertiary amylimido tris(dimethylamide), which comprises allowing 1 mole of tantalum pentachloride, 4 moles of lithium dimethylamide and 1 mole of lithium tertiary amylamide to react with one another in an organic solvent, then separating a byproduct lithium chloride by filtration, distilling the solvent away, and distilling the residue in vacuo.

According to still another aspect of the present invention, there is provided a solution of starting material for MOCVD, comprising at least 10 wt % organic solvent added to tantalum tertiary amylimido tris(dimethylamide).

According to still another aspect of the present invention, there is provided a method of forming a tantalum nitride film by the MOCVD method wherein tantalum tertiary amylimido tris (dimethylamide) is used as the starting material.

DETAILED DESCRIPTION OF THE INVENTION

Figure 1:
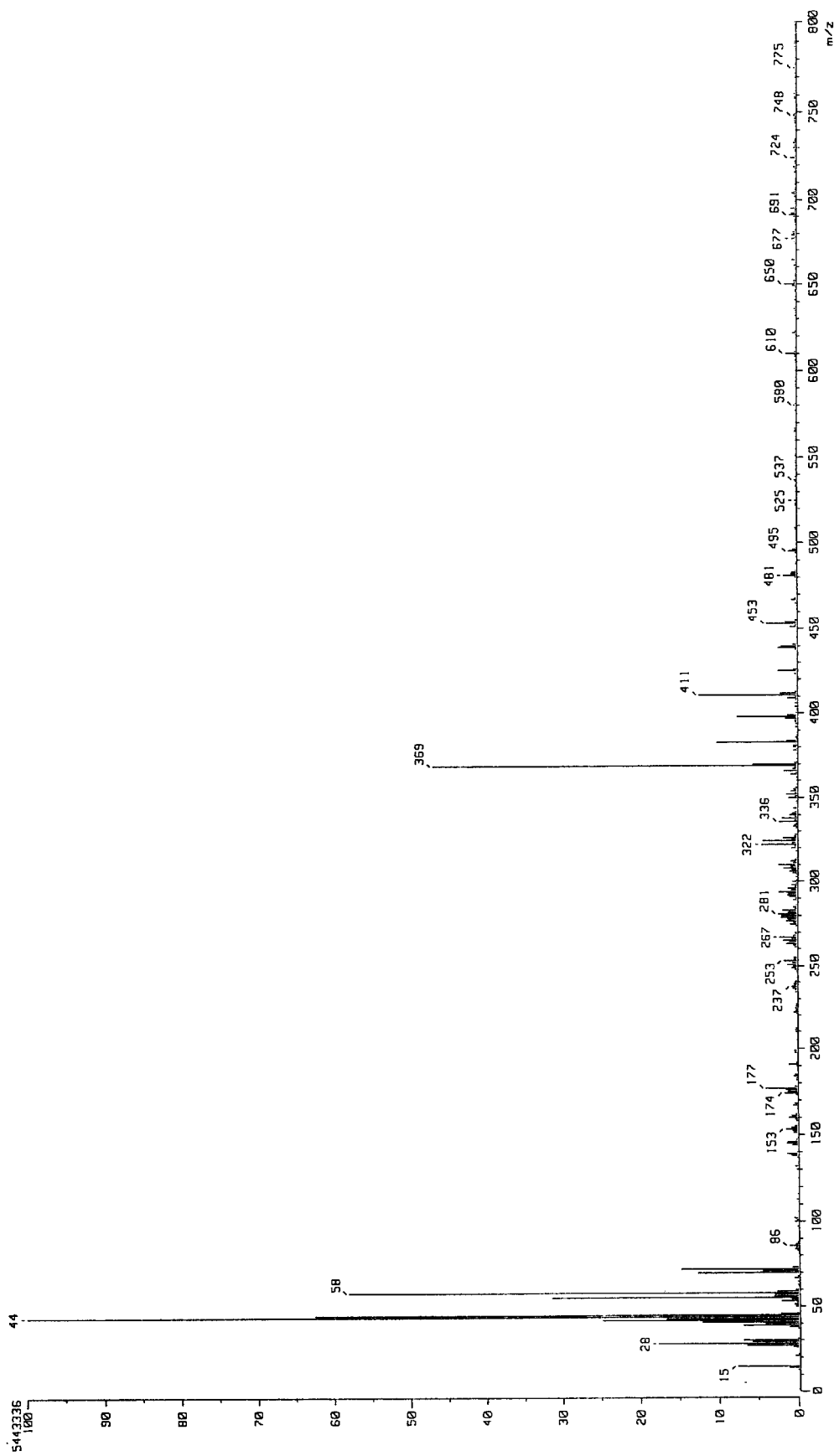
FIG. 1 shows the result of measurement of Ta(NtAm)(NMe$_2$)$_3$ by EI-MS.

The tantalum tertiary amylimido tris(dimethylamide) of the present invention is a novel compound (referred to hereinafter as Ta(NtAm)(NMe$_2$)$_3$. This compound can be produced according to a process for producing Ta(NtBu)(NMe$_2$)$_3$ as described by William A. Nugent, Inorg. Chem., vol. 22, 965 (1983).

Four moles of lithium dimethylamide and 1 mole of lithium tertiary amylamide are suspended and dissolved in hexane, and powdery tantalum pentachloride is added thereto under stirring and cooling with water, and the mixture is reacted for 2 days at 10 to 40° C. Then, lithium chloride crystals formed as byproduct are removed by filtration, and from the resulting yellow liquid, low-boiling components such as solvent etc. are distilled away under reduced pressure. As a result, an orange viscous liquid remains, and this product is distilled under reduced pressure at 1 Torr, whereby a yellow liquid is obtained in the vicinity of 90° C. This liquid is recrystallized from hexane at −30° C., and the resulting pale yellow crystals are subjected to distillation in vacuo at 1 Torr, and a pale yellow liquid is obtained as a major distillate at about 80° C. This liquid turns pale yellow solid at room temperature. The yield is 61% based on tantalum pentachloride.

Lithium dimethylamide used as the starting material is obtained in a white-yogurt state by reacting a solution of n-butyl lithium in hexane with a dimethylamine gas. Lithium tert-amylamide is obtained in a white-suspension form by reacting a solution of n-butyl lithium in hexane with tert-amylamine. These two reaction solutions may be combined for use. As the reaction solvent, it is possible to use not only hexane but also heptane, octane, toluene, diethyl ether and THF.

If tantalum pentachloride used is a high-purity commercial product, the finally formed product has less impurities of metal elements. As a matter of course, the reaction rate and the increase in the reaction temperature are influenced depending on the grain size of tantalum pentachloride, and thus the rate of adding the same is regulated. The reaction time is 5 to 50 hours.

One mole of tantalum pentachloride is charged with 4 moles of lithium dimethylamide and 1 mole of lithium tert-amylamide, but lithium dimethylamide and lithium tert-amylamide may be added in slight excess.

The identification results and physical properties of Ta(NtAm)(NMe$_2$)$_3$ obtained in Example 1 are described below.

(1) Analysis of the Composition

The result of ICP atomic emission spectroscopic analysis of a solution formed by decomposing the compound in a wet system is as follows:

Found: 45.9 wt % Ta (theoretical: 45.4 wt %) Analysis of C, H, and N: C: 32.8 (theoretical, 33.2 wt %), H: 7.2 (theoretical, 7.4 wt %), N: 13.5 (theoretical, 14.1 wt %), (2) Analysis of Impurities The result of ICP emission spectroscopic analysis (unit: ppm) is as follows:

Al<1, Ca<1, Fe<1, Mg<1, Ti<1, and Li<1, thus indicating high purity.

Analysis of total Cl indicated that Cl was 4 ppm.

(3) EI-MS

Measurement Conditions

Unit: JEOL AX505W

Ionization method: EI

Ionization-source temperature: 230° C.

Ionization energy: 70 eV

The measurement result is shown in FIG. 1.

There are two isotopes of Ta, but taking it into consideration that 99.99% is $^{181}$Ta, major m/z values and their corresponding strength (%) and ion species are shown below: m/z=411 (12%) Ta [NC(CH$_3$)$_2$C$_2$H$_5$] [N(CH$_3$)$_2$]$_2$ [N(CH$_3$)(C$_2$H$_5$)] or Ta [NC(CH$_3$)$_2$CH(CH$_3$)$_2$] [N(CH$_3$)$_2$]$_3$ 398 (7%) Ta [NC(CH$_3$)$_2$C$_2$H$_5$] [N(CH$_3$)$_2$]$_3$ molecular ion 383 (10%) Ta [NC(CH$_3$)C$_2$H$_5$] [N(CH$_3$)$_2$]$_3$ 369 (47%) Ta [NC(CH$_3$)$_2$] [N(CH$_3$)$_2$]$_3$ 58 (58%) C$_4$H$_{10}$ or N(CH$_3$)(C$_2$H$_5$)

44 (100%) N(CH$_3$)$_2$ (4) $^1$H-NMR

Measurement conditions:

Unit: BRUKER AC300P (300 MHz)

Solvent: C$_6$D$_6$

Method: 1D

Figure 2:
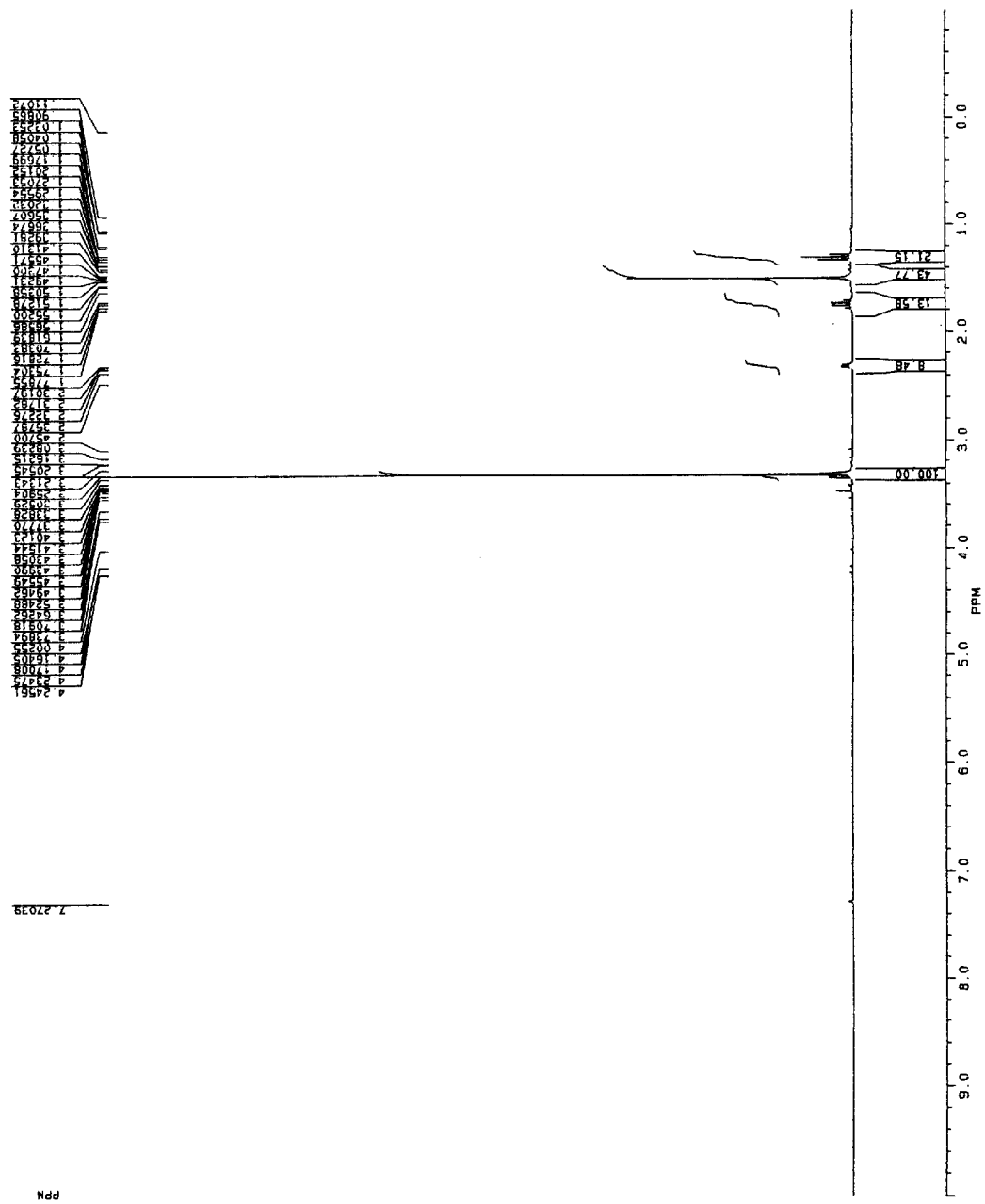
FIG. 2 shows the result of measurement of Ta(NtAm)(NMe$_2$)$_3$ by $^1$H-NMR.

The measurement result is shown in FIG. 2.

$\delta_H$ (ppm) and (assignment) are shown below: 3.31 s (18H, N(CH$_3$)$_2$), 2.30 d (1.5H, not clear), 1.75 q (2.4H, CH$_3$CH$_2$C(CH$_3$)$_2$N), 1.49 s (7.9H, CH$_3$CH$_2$C(CH$_3$)$_2$N), 1.30 t (3.8H, CH$_3$CH$_2$C(CH$_3$)$_2$N), (5) FT-IR Measurement conditions:

Unit: SHIMADZU FT-IR8600

Method: KBr method

Resolution: 4.0 cm$^{-1}$

Figure 3:
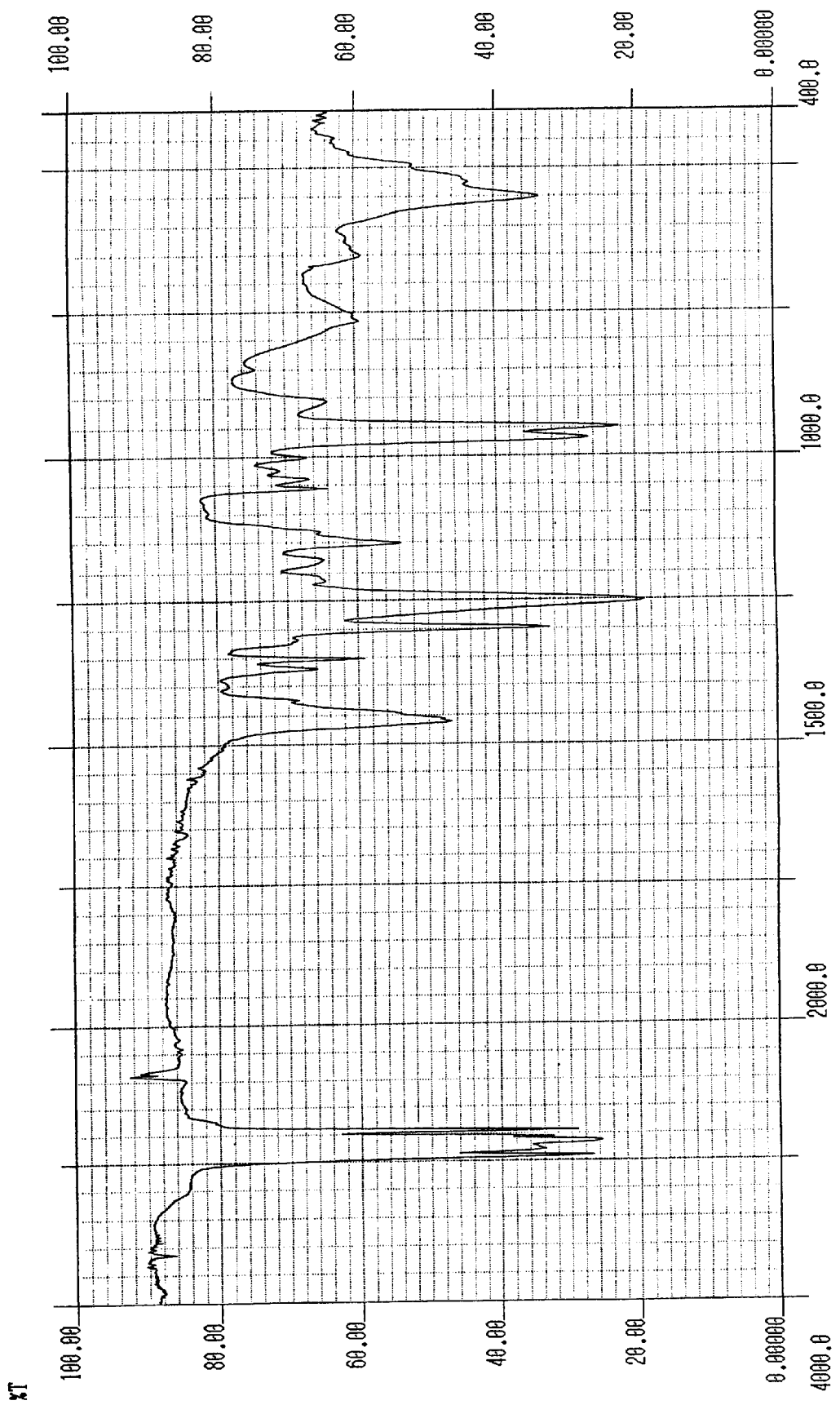
FIG. 3 shows the result of measurement of Ta(NtAm)(NMe$_2$)$_3$ by FT-IR.

The measurement result is shown in FIG. 3. Spectrum (cm$^{-1}$):

3655, 2964, 2916, 2855, 2824, 2775, 2397, 2349, 1462, 1423, 1371, 1352, 1319, 1298, 1252, 1215, 1178, 1151, 1130, 1057, 1040, 1024, 1001, 968, 949, 907, 768, 652, 550

(6) Vapor Pressure

1 Torr/80° C. from data on distillation thereof.

(7) State and Melting Point

It was pale yellow crystals and its melting point was 36° C.

(8) TG-DTA

Measurement conditions:

Sample weight: 12.51 mg

Atmosphere: Ar, 1 atmospheric pressure

Heating rate: 20.0 deg/min

Figure 4:
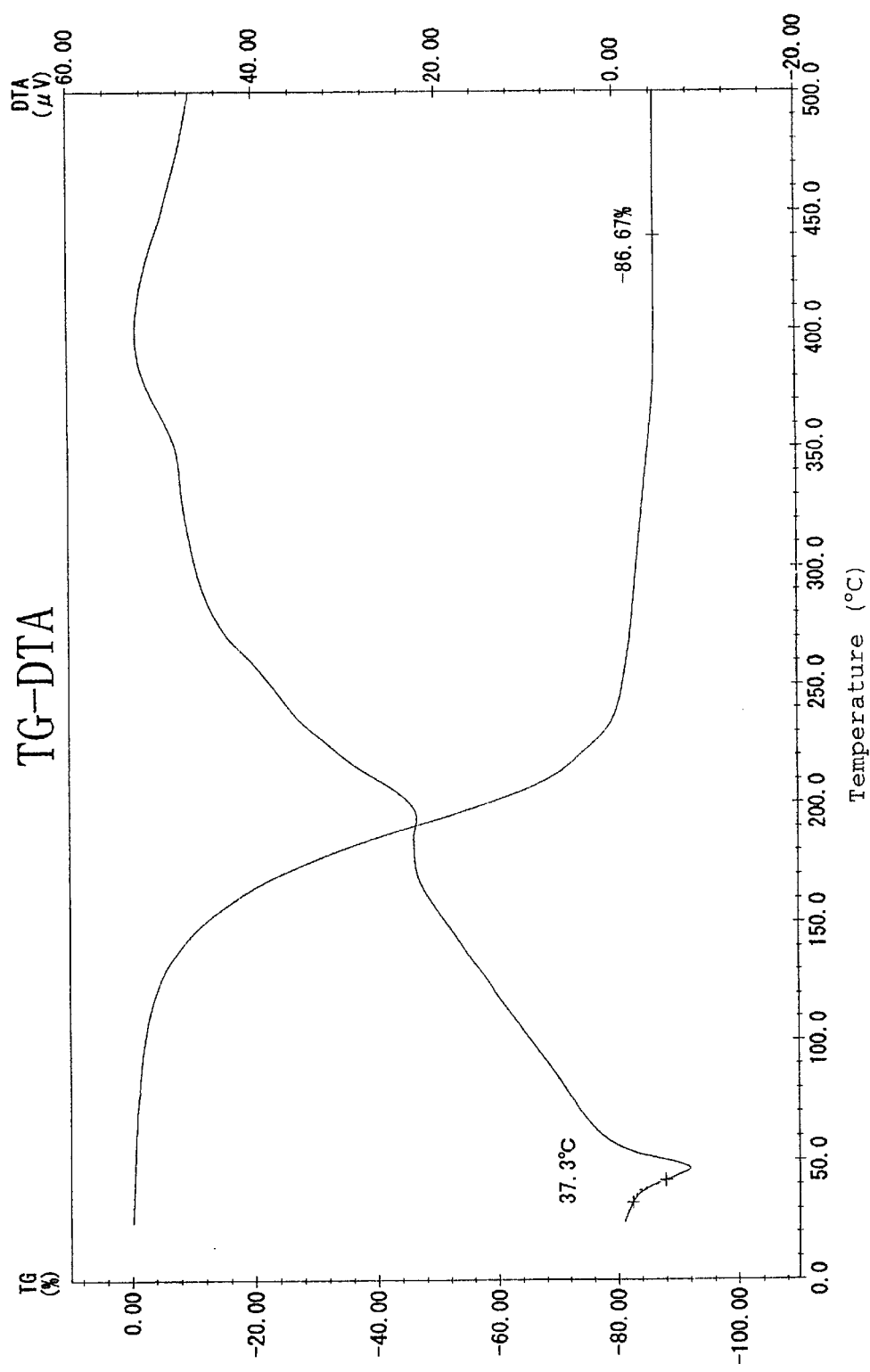
FIG. 4 shows the result of measurement of Ta(NtAm)(NMe$_2$)$_3$ by TG-DTA at 1 atmospheric pressure.

The measurement result is shown in FIG. 4.

(9) Conversion Thereof into a Solution

Ta(NtAm)(NMe$_2$)$_3$ was completely dissolved in hexane at 20° C. to give 10 wt % organic solvent solution without forming any precipitates. This compound was dissolved in toluene as well in the same manner as above.

This compound was identified as Ta(NtAm)(NMe$_2$)$_3$ on the basis of the results of mainly the determined composition and analysis thereof by EI-MS, $^1$H-NMR and FT-IR described above.

Then, the known compounds Ta(NtBu)(NEt$_2$)$_3$ and Ta(NtBu)(NMe$_2$)$_3$ were synthesized in the same manner as for Ta(NtAm)(NMe$_2$)$_3$, and their melting point and vapor pressure were determined and compared with those of the present compound Ta(NtAm)(NMe$_2$)$_3$.

The results of melting point and vapor pressure are shown in Table 1.

TABLE 1

| Compound | Melting point (° C.) | Temperature (° C.) giving 1 Torr |
|---|---|---|
| Ta(NtAm)(NMe$_2$)$_3$ | 36 | 80 |
| Ta(NtBu)(NEt$_2$)$_3$ | Liquid at room temp. | 130 |
| Ta(NtBu)(NMe$_2$)$_3$ | 69 | 70 |

As can be seen from Table 1, the temperature at which the Ta(NtAm)(NMe$_2$)$_3$ of this invention gives 1 Torr is 80° C. which is lower by about 50° C. than 130° C. for Ta(NtBu)(NEt$_2$)$_3$. Further, the vapor pressure of Ta(NtBu)(NEt$_2$)$_3$ at 80° C. is as low as 0.1 Torr, and when compared at the same temperature, the vapor pressure of the Ta(NtAm)(NMe$_2$)$_3$ of this invention is about 10 times as high as that of Ta(NtBu)(NEt$_2$)$_3$. Accordingly, it is evident that as the starting material in CVD, the Ta(NtAm)(NMe$_2$)$_3$ of this invention has very preferable properties in respect of vapor pressure. Therefore, the present compound can be vaporized at a lower source temperature and at a lower temperature of a gasification unit, thus undergoing less heat deterioration, being stable during use and reducing particles generated.

As can be seen from the result of TG-DTA in FIG. 4, the Ta(NtAm)(NMe$_2$)$_3$ of this invention is well gasified, and thus the residue remaining after vaporization is as low as 13.3% at 450° C., and thus the compound is relatively stable to heat.

According to the result of EI-MS in FIG. 1, there is a major peak of a fragment with m/z=369 estimated to contain Ta=N bond, suggesting that the present compound forms TaN relatively easily.

The Ta(NtAm)(NMe$_2$)$_3$ of this invention is of high purity with 1 ppm or less metal element impurities and 4 ppm Cl. Its melting point is 36° C. which is slightly higher than room temperature, so that attention should be paid so as not to solidify the compound. Its purity can be further raised by refining through distillation.

The present invention also relates to a method of forming a tantalum nitride film by the MOCVD method, wherein Ta(NtAm)(NMe$_2$)$_3$ is used as the starting material.

The method of feeding Ta(NtAm)(NMe$_2$)$_3$ is as follows:
① While the source temperature is kept at 50 to 120° C., the compound is fed at the self-pressure of its generated vapor by a vapor source mass flow controller;
② Ta(NtAm)(NMe$_2$)$_3$ is liquefied by keeping the source temperature at a temperature higher than the melting point of 36° C., preferably at 40° C. or more, followed by gasification thereof by bubbling with a carrier gas;
③ The compound is liquefied by increasing the source temperature to 40° C. or more, and the resultant liquid is fed by a liquid mass flow meter heated at about 50° C. and then gasified in a gasification unit; and
④ Ta(NtAm)(NMe$_2$)$_3$ is dissolved at room temperature in 10 wt % or more organic solvent, and the resultant solution is fed by a liquid mass flow controller or a liquid flow mass flow meter at room temperature, and then gasified in a gasification unit.

Ta(NtAm)(NMe$_2$)$_3$ in a liquid form has a viscosity of 10 to 20 cp, to which bubbling, a mass flow controller or a mass flow meter can be applied. The organic solvent in ④ can make use of conventional solvents for use in the starting material in CVD, such as hexane, heptane, octane and butyl acetate.

The substrate can make use of SiO$_2$/Si to form copper paths for electric current thereon.

The tantalum nitride film can be formed by thermal CVD wherein Ta(NtAm)(NMe$_2$)$_3$ is brought into contact with a substrate at a temperature of 450 to 650° C. under reduced pressure at $10^{-2}$ to 1 Torr. The tantalum nitride film obtained on the substrate having a higher temperature is cubic TaN according to XRD. Accordingly, it is low resistant. Adhesion of the tantalum nitride film to the SiO$_2$/Si substrate is also good. Only Ta(NtAm)(NMe$_2$)$_3$ may be introduced into the CVD chamber, but if necessary an ammonia gas may be supplied.

EXAMPLES

Example 1

Production of Ta(NtAm)(NMe$_2$)$_3$

A 500-mL three-necked Erlenmeyer flask equipped with a thermometer and a stirrer was evacuated and replaced therein by an argon atmosphere, and 150 mL fresh LiNMe$_2$ suspension in hexane (20.4 g or 0.40 mol LiNMe$_2$) and 50 mL fresh LiNHtAm suspension in hexane (9.3 g or 0.10 mol LiNHtAm) were introduced into the flask and stirred well for 1 hour. While the flask was cooled with water, powdery high-purity TaCl$_5$ (35.8 g, 0.10 mol) was gradually added thereto such that the temperature of the reaction solution became 20 to 35° C. Thereafter, the mixture was stirred at room temperature for 48 hours, to form slurry with good sedimentation properties. After LiCl particles formed as byproduct were separated by filtration, a yellow transparent liquid was obtained. This liquid became an orange viscous liquid by allowing the solvent hexane and amines formed as byproducts to be distilled away under reduced pressure on an oil bath at a temperature of 30° C. This liquid was subjected to distillation at about 90° C. at 1 Torr to give 28.3 g yellow transparent liquid. This liquid was dissolved in 30 ml hexane and re-crystallized therefrom at −30° C. The resulting pale yellow crystals were subjected to distillation at 1 Torr, and 24.3 g colorless liquid was obtained as a major distillate at a distilling temperature of about 80° C. This liquid was solidified at room temperature into pale yellow needle crystals. As a result of identification as described above, the resultant product was Ta(NtAm)(NMe$_2$)$_3$ (0.061 mol) and the yield was 61% based on TaCl$_5$.

Example 2

Formation of TaN Film by CVD Method Using Ta(NtAm)(NMe$_2$)$_3$

A cylinder containing Ta(NtAm)(NMe$_2$)$_3$ obtained in Example 1 was heated at 110° C., and the generated vapor was introduced at the self-pressure thereof via a vapor source mass flow controller into a CVD chamber of cold wall type. The CVD chamber was kept at 0.05 Torr in an exhaust system, and the vapor was thermally decomposed and accumulated on a SiO$_2$/Si substrate at 550° C. After an about 100-nm film was formed, the film was measured with XRD, indicating that the film was cubic TaN.

Example 3

In Example 2, a cylinder containing Ta(NtAm)(NMe$_2$)$_3$ was kept at 50° C. to liquefy the Ta(NtAm)(NMe$_2$)$_3$, then the resultant liquid was introduced via a liquid mass flow meter heated and kept at 50° C., and the whole of the liquid was gasified in a gasification unit at 120° C. and then introduced into a CVD chamber. The same procedure as in Example 2 was conducted in the subsequent process, whereby a cubic TaN film could be formed.

Example 4

Ta(NtAm)(NMe$_2$)$_3$ was converted at room temperature into a solution by adding 10 wt % hexane, then the resultant solution was introduced via a liquid mass flow controller, and the whole of the solution was gasified in a gasification unit at 120° C. and then introduced into a CVD chamber. The same procedure as in Example 2 was conducted in the subsequent process, whereby a cubic TaN film could be formed.

INDUSTRIAL APPLICABILITY

The Ta(NtAm)(NMe$_2$)$_3$ of the present invention is a novel compound having a vapor pressure that is 10 times as high as that of known Ta(NtBu)(NEt$_2$)$_3$ at the same temperature.

Accordingly, the present compound can supply a large amount of vapor easily in mass-production CVD. This compound can be easily purified to high degrees by re-crystallization and distillation, and thus it is preferable as a starting material in CVD for semiconductor devices. In addition, this compound has a melting point of 36° C., and therefore it can be liquefied by slight heating and thus stably supplied by a liquid mass flow controller.

By subjecting this Ta(NtAm)(NMe$_2$)$_3$ on a SiO$_2$/Si substrate to thermal CVD, a cubic TaN film of low resistance can be formed.

What is claimed is:

1. Tantalum tertiary amylimido tris(dimethylamide).

2. A process for producing tantalum tertiary amylimido tris(dimethylamide), which comprises allowing 1 mole of tantalum pentachloride, 4 moles of lithium dimethylamide and 1 mole of lithium tertiary amylamide to react with one another in an organic solvent, then separating a byproduct lithium chloride by filtration, distilling the solvent away, and distilling the residue in vacuo.

3. A solution of starting material for MOCVD, comprising at least 10 wt % organic solvent added to tantalum tertiary amylimido tris(dimethylamide).

4. A method of forming a tantalum nitride film by the MOCVD method wherein tantalum tertiary amylimido tris(dimethylamide) is used as the starting material.

* * * * *